United States Patent [19]
Hansson

[11] Patent Number: 4,698,305
[45] Date of Patent: Oct. 6, 1987

[54] METHOD OF TREATING WOOD

[76] Inventor: Göran Hansson, Oras 11, 242 00 Hörby, Sweden

[21] Appl. No.: 652,487

[22] Filed: Sep. 20, 1984

[30] Foreign Application Priority Data

Sep. 20, 1983 [SE] Sweden ................................ 8305055

[51] Int. Cl.⁴ ........................ C12P 1/02; C12R 1/645; C12N 1/22; C12N 1/14

[52] U.S. Cl. .................................... 435/171; 435/252; 435/254; 435/911

[58] Field of Search ............... 435/171, 267, 277, 911, 435/244, 254, 252; 162/1, 9

[56] References Cited

U.S. PATENT DOCUMENTS 2,671,751 3/1954 Kunz et al. .......................... 435/277
4,346,175 8/1982 Enfors et al. .................. 435/277 X

FOREIGN PATENT DOCUMENTS 0001540 4/1979 European Pat. Off. .

OTHER PUBLICATIONS

Pirt, S. J., *Principles of Microbe and Cell Cultivation,* Blackwell Scientific Publications, Oxford, England, 1975, pp. 143–144.
Naik, B. N. et al, *Geobios,* vol. 10, 1983, pp. 218–222.
Perrin, P. W., *Mycologia,* vol. 71, 1979, pp. 867–869.
Karlson, P. et al, *Introduction to Modern Biochemistry,* Academic Press, N.Y., 1968, pp. 171 and 214.
Gemant, A., *Molecular Biology Reports,* vol. 1, 1974, pp. 257–261.
Kobayashi, H. et al, *J. Ferment. Technol.,* vol. 50, No. 9, 1972, pp. 625–632.
Sumner, J. L. et al, *Can. J. Microbiol.,* vol. 15, 1969, pp. 515–520.

*Primary Examiner*—Esther M. Kepplinger
*Assistant Examiner*—Jeremy M. Jay
*Attorney, Agent, or Firm*—Dennison, Meserole, Pollack & Scheiner

[57] ABSTRACT

Method of effecting zoning in wood with the aid of fungus cultures. The wood is pretreated by sterilizing it, setting a suitable moisture content and impregnating it. Impregnation with nutrients ensures that the fungi are sustained by the nutrients added and not by the wood. Special patterns can be achieved by using inhibitors.

Pretreated wood is inoculated with one or more fungus cultures and stacked in sandwich fashion. An interlayer is inserted into the inoculated sandwich to produce the desired zoning pattern.

Incubation is performed with controlled moisture contents and moisture gradients in the wood, as well as the composition of the gas phase, and may be carried out as a two-step process.

The method is performed entirely or partially in a closed system.

26 Claims, 10 Drawing Figures

METHOD OF TREATING WOOD

Figure 1:
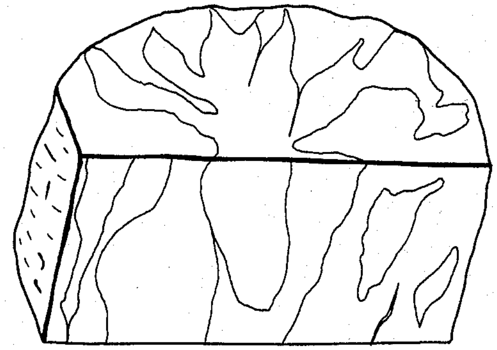

The present invention relates to a method of manufacturing zoned wood with the aid of fungi. The appearance of most types of wood can be altered by various types of pigmentation. The altered appearance may include dots, streaks, patches and what is known as zoning. The causes of these alterations may be of a chemical or biological nature, which as chemically caused discolouring, e.g. oxidation of certain components in the wood by oxygen from the air, or precipitation of iron tannate or copper tannate in wood, such as discolouring fungus, e.g. discolouring fungus or other lower fungi causing patches or streaks in different tones, such as mould fungus which gives superficial changes in colour by producing large quantities or spores on the surface of the wood, or decomposing fungi which result in deeply penetrating discolouration against white or brown when the wood is attached by white or brown rot fungi respectively.

The natural occurrence of zoned wood is well known. This type of wood is obtained when deciduous trees, e.g. beech and birch, are attacked and decomposed by certain types of higher fungi. Zoned wood has also been described in scientific literature, the first article being published as long ago as 1878, by Hartig.

Zoned wood, thus, is wood in the process of being decomposed by higher fungi, generally white-rot fungi. The wood can be considered as being filled with a number of separate mycelium areas, the fungi forming a dark "film" in the boundaries between these areas. This film comprises wood filled with abnormally swollen and pigmented fungus hyphae and forms what is known as a zone surface or zone plate. The zone surfaces may serve as a physical limit to adjacent mycelium areas or to an unsuitable environment. When a piece of zoned wood is sawn, the zone surface will emerge as zone lines in the cut surfaces. The zone lines form a mosaic, the density and appearance depending on the type of fungus (fungi), the time, structure of the wood and environmental factors (Picture 1).

In older literature, the concepts of zone lines, zone surfaces, zoned wood, etc. on the one hand are sometimes confused with other types of colour changes in the wood. In recent literature, however, zoned wood is defined as wood filled with the above-mentioned "films" of abnormally swollen and pigmented fungus hyphae. These are produced by specific biological process, see below. Other types of colour changes include, for instance, the formation of pigment which can diffuse and appear in the wood in the form of dots, patches or streaks or the formation of dark bands containing resin and glue substances produced by oxidation of wood-decomposing products. However, these types of colour alterations have a completely different appearance and are produced in totally different ways from zone wood.

Innumerable fungi are capable of causing zoning in wood. The best known and most studied are *Armillaria mellea* and *Xylaria polymorpha.*

The natural occurrence of zoned wood takes a considerable time, often many years. During this time the fungal attack on the wood structure often becomes advanced and the zoned wood is therefore often porous in structure.

Although literature on zoning has long been available, exactly how the zoning occurs is still unclear.

There are probably several different mechanisms and several different types of zone lines.

It has been shown that certain types of zoning are produced in the contact surface between antagonistic mycelia. In such cases the zone surfaces form a boundary between genetically different mycelium units.

Zoning may also be produced by a uniform mycelium, without antagonism. In this case, the zoned wood consists of a mosaic of attached and nonattacked sections, separated by zone surfaces. The mechanisms behind this and the reasons for only certain parts of the wood being attacked are not known. A reasonable assumption is that, by forming zones, the fungus is able to isolate is mycelium from unsuitable environmental factors.

Two methods of producing zoned wood by inoculating wood with fungus cultures have been described in the literature.

A. Method based on several cultures

When several fungi grow on the same substrate, various interactions may occur: e.g. the fungus mycelia may mix freely or one mycelium may overcome the others. "Dead-lock" structures often occur, giving rise to coloured contact zones between mycelia. Inoculating wood with certain combinations of two or more antagonistic fungi of different type (interspecific antagonism) may therefore cause zoning. It has also long been known that zone surfaces often separate different types of fungus in certain forms of zoning occurring naturally.

Zoning caused by intraspecific antagonism also occurs naturally, but it is only recently that this is starting to be understood. Intraspecific antagonism, particularly between different branches of Coriolus versicolor, has been thoroughly studied. This technique can be reproduced in the laboratory and a wood material similar to "naturally zoned wood" can be obtained. This process is presumably similar to that occurring naturally. This also applies to the time required—incubation times of 1–2 years are necessary to obtain zoned wood by this method.

B. Method based on a single culture

This method is used primarily when working with *Armillaria mellea,* but also to a certain extent with *Xylaria polymorpha* and some Fomes and Polyporus types. Beech and birch are usually used, either as whole pieces of branch with the bark still on, or small blocks of wood which have been sawn out. The wood is infected with a pure culture and is incubated in a suitable environment for 3–12 months. When the wood is cut, a zone surface is often found some mm below the surface, see FIG. 2. If the block of wood, incubated and penetrated by fungus, is sawn into pieces and the pieces then incubated once more (1–4 weeks), new zone surfaces will be formed just below the newly exposed surfaces, see FIG. 2. In this figure 1 denotes zone lines after the first incubation and 2 denotes zone lines after the second incubation. This method of producing zoned wood has several drawbacks: (1) it is relatively time-consuming (2) zoning is obtained only close to the surfaces of the wood and not as a mosaic, and (3) it is unsuitable from a practical point of view.

In a procedure already known (Swedish Pat. No. 407758) the use of specially selected micro-organisms is proposed, primarily the *Armillaria mellea* and *Xylaria polymorpha* fungi and *Bacillus polymyxa* bacteria or enzymatically active preparations of these organisms. It is suggested that these be inoculated onto deciduous wood and incubated under suitable environmental conditions, to obtain the desired modification of the wood. Modification here implies increased porosity and the production of colour pigment, the release of resin and glue substances from the wood and the production of acid metabolism and decomposition products. However, the patent offers no new information as to the method of producing zoned wood.

Fungus attacks on wood are generally considered as negative and detrimental to the properties of the wood. However, some methods and patents exist relating to influencing wood with the aid of fungi in order to obtain a material with certain desired properties.

In the "Mykoholz process" a wood material is produced, with the aid of *Pleurotus ostreatus* and *Trametes versicolor* fungi, the wood having low specific weight, high porosity and reduced strength (German Pat. No. 946 845). This mykowood has a limited field of application, e.g. in pencils and as wood for models.

The use of fungi, i.e. *Chlorosplenium seruginosum,* to give wood in the form of blocks, planks or veeer an attractive appearance as well as protection against rot, was patented as early as early as 1913 (British patent No. 24 595). Even other fungi such as Trichoderma and Scytalidium can be used for biological control of damage caused by rotting. Intentional infection of wood with these fungi can prevent or delay damage caused by rot fungi.

The Swedish patent mentioned above proposes the use of e.g. *Armillaria mellea* and *Xylaria polymorpha* to produce a modified wood. A particular application suggested is veneered products such as loud-speaker boxes.

As to the production and use of zoned wood, the work described in the literature is more in the nature of foundation-laying rather than being applied technically. Often the object is to study the structure of the fungi population and dynamics of the wood or the interaction between pathogenic and non-pathogenic fungi in wood. No. practical use has been suggested for zoned wood of this type. On the other hand, naturally zoned wood, primarily beech, is used to a limited extent in Sweden nowadays. It is mainly the aesthetic properties of zoned wood which are utilized here, for instance for making bowls.

If zoned wood is to be used on a larger scale, e.g. in the furniture and wooden floor industries, new technology is required for its controlled production.

The demands on such new technology are substantially the following:

Zoning must be possible in both veneers and thicker wood, in both fresh and dried wood, and in several different types of wood, particularly beech and birch.

These must be a suitable method of pretreating wood, particularly with respect to necessary disinfection, sterilization and control of the moisture content.

There must be an economic way of producing active inoculation material.

Zoning should be possible, preferably using only one fungus. However, it should be possible to use several different fungi in order to obtain different types of zone lines.

Incubation should be performed in a closed system keeping a check on environmental parameters (temperature, moisture, gas phase, etc.).

The process must be quick, with a maximum incubation time of 1-2 months.

It must be possible to control the process to give different types of zoning patterns.

The method must give sufficient penetration of the zone surfaces, enabling the wood to be ground or given some other surface treatment.

The zone pattern must be resistant to light, chemicals, etc.

It must be possible to check for infection, particularly mould infections.

The process shall be controlled, stable and result in little waste.

Production of zoning must be possible without any great effect on the strength or porosity of the wood.

Suitable technology must be available to discontinue the process.

It must be possible to scale up the process.

The present invention relates to a practically functioning method of producing zoned wood under the above controlled conditions.

The method has been developed using primarily birch, but beechwood and ashwood have also been found suitable for zoning. Thinly sawn slices (1-3 mm) and veneer (0.6 mm) have mosly been used, but some thicker wood also. Both fresh and dried wood has proved suitable for zoning.

Figure 3:
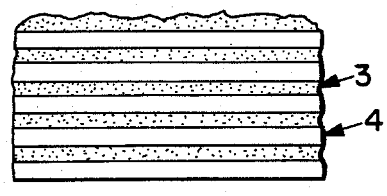
Figure 2:
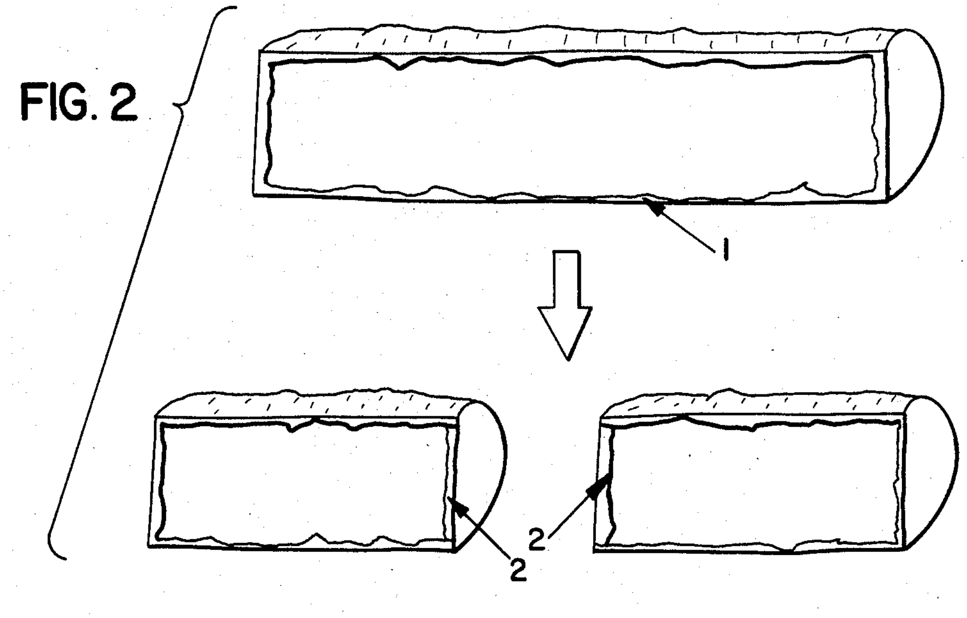
Figure 5:
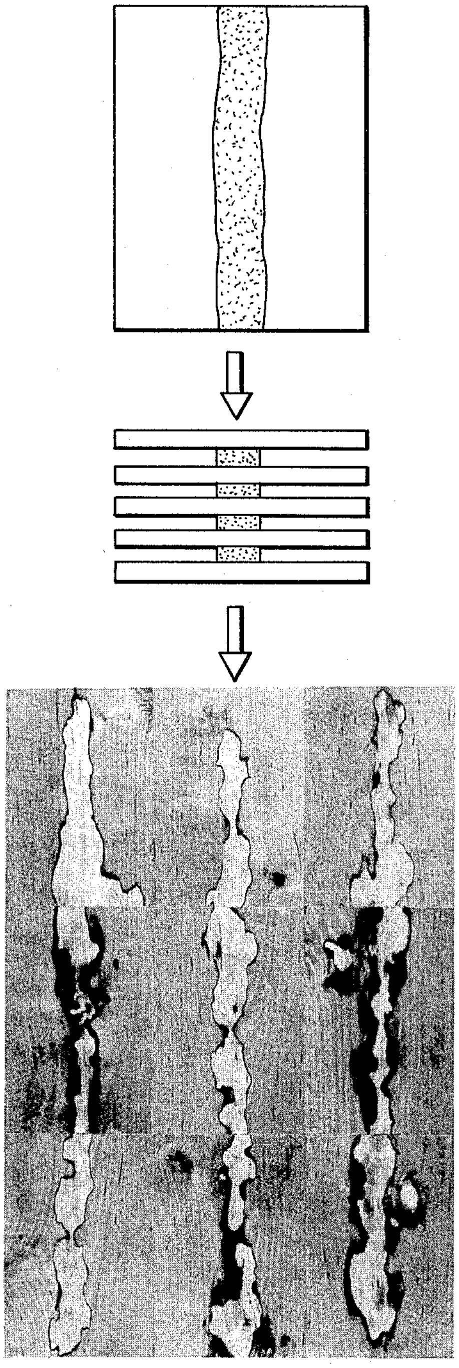
Figure 6:
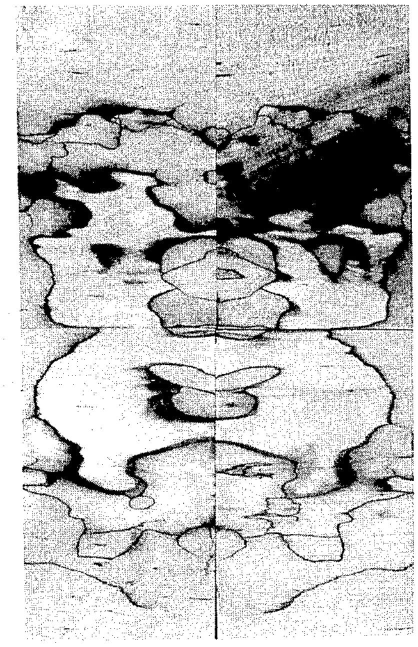
Figure 7:
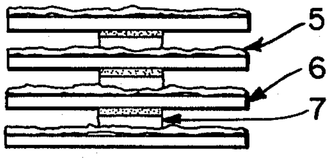
Figure 8:
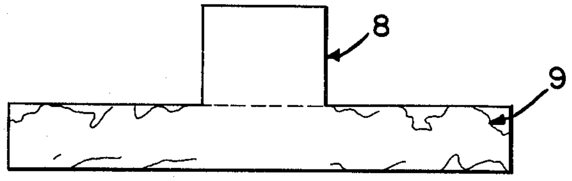
Figure 10:
Figure 9:
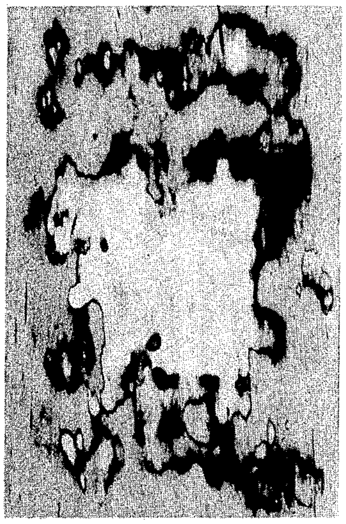

In the following the method will be described with reference to the enclosed drawings in which FIG. 1 shows a section of zoned wood, FIG. 2 shows technology for inducing zoning in wood, FIG. 3 shows inoculation of wood in accordance with the sandwich method, FIG. shows point-inoculation of birch, FIG. 5 shows streak-inoculation of birch, FIG. 6 shows zoning patterns with pairs of mirror-images on birch, FIG. 7 shows inoculation of a sandwich with interlayer, FIG. 8 shows a section through a piece of wood, zoned in a sandwich with interlayer, FIG. 9 shows a block of wood, sandwich-zoned with square interlayer, and FIG. 10 shows in detail a network pattern of zone lines on birch.

Suitable pretreatment of the wood has been found to be of fundamental importance to the zoning process. It is particularly necessary for the wood to be free from infection by micro-organisms which affect the zoning process and also for it to have a correct moisute content. The method of disinfection/sterilization is not critical; steam at atmospheric or increased pressure, dry heat, radiation (gamma, UV, IR) or gas-sterilization with ethylene oxide, for instance, have been tested and found suitable. However, controlling the moisture content of the wood has proved difficult, particularly in the case of thin wood with a large area in contact with the air and little moisture-retaining ability. By "moisture content" is meant the weight of water in relation to the weight of dry wood. The wood can be sterilized throughout its thickness or only on the surface, by one of the above methods. Alternatively the wood may be treated with anti-microbial substances to prevent infection.

A method has been developed for preparing sterile wood with an extremely accurately set moisture content:

- the starting material is dry or moist wood with known moisture content.
- the required quantity of water is added, in a suitable container, to give the wood the desired moisture content, the moisture content being first determined for the specific fungus being used.

by means of vacuum-treatment in a moist environment, the water is absorbed and distributed throughout the wood structure.

the wood is wrapped tó make it air-tight.

sterilization by various methods may be performed before or after this process.

This method enables a stock of durable wood to be built up, ready for inoculation. This is extremely desirable since, for instance, the composition (water content, nutrient content) of timber felled at different seasons of the year varies considerably.

The desired moisture content can also be achieved by immersing the wood in water at atmospheric pressure or at reduced/increased prèssure, for a standard length of time to allow the desired quantity of water to be absorbed, or by steam treatment for a standard period.

It would be desirable to obtain zoning in wood without the wood being decomposed and various strength properties thereby being deteriorated. In naturally formed zone wood, however, zoning is associated with the fungus growth and thus decomposition of the wood. In conjunction with the invention, however, it has been found that when fungi grow on vermiculite (inert material) impregnated with liquid nutrient solution, zoning occurs in any case, despite the absence of wood. According to one embodiment of the method according to the invention, the wood is impregnated, prior to inoculation, with suitable nutrient solution and the fungus grows on this nutient and, under suitable environmental conditions, produces zoning in the wood. There is thus no decomposition of the wood, or only neglible decomposition, and the wood will therefore serve as a "matrix" for the zoning. The wood has been impregnated with pH/redox-active substances which promote the growth of the fungus in order to obtain quick establishment of the fungus. The wood may also be impregnated with substances stimulating the ability of the fungus to produce zoning, e.g. precursors of the fungus pigment, and control the appearance of the zoning.

In other embodiments of the invention impregnation has been performed with substances preventing the fungus from attacking the wood, e.g. hydrophobic substances or inhibitors. These substances can be applied on certain parts of the wood surfaces in a desired pattern in order to control growth of the fungus and zoning to only the other parts of the wood surfaces.

Substances preventing infection by other organisms, particularly mould infections, may be used at the impregnation stage. Suitable compositions are Benomyl and certain antibiotics, for instance.

As mentioned above, it is already known that a great number of fungi have the ability to produce zoning in wood. The classical organism *Armillaria mellea* has mainly been used in this work, but other types of fungi have been tested and *Phellinus igniarius* and *Phellinus pini* have been found to produce zoning, partially of a different appearance from that produced by Armillaria.

In the work with Armillaria reported in literature colonies cultivated on agar areas in air have been used as inoculation material. In the present method, on the other hand, submerse fermentor cultivation is used for production of the inoculation material. Such a method is more suitable for production on a large scale. However, the conventional fermentor cultivation method, i.e. using impeller-stirred tank reactors, gives a very slow growth of Armillaria, probably due to excessive shearing forces in the liquid phase. For this reason a method has veen developed based on cultivation in air-lift fermentors. Using this method large quantities of inoculation material can be produced very quickly (ca. 1 week). The fungus grows in the form of "pellets" and homogenization of the material may be desirable. The suspension obtained is easy to use, keeps well under refrigeration and is suitable for spreading on the surface of wood.

A new method of inoculating sheets of wood, known as sandwich-inoculation, has been developed, see FIG. 3. In the figure, 3 denotes inoculation material and 4 a sheet of wood.

According to conventional technology, fungus is inoculated onto the surface of pieces of wood. A surface colony is thus formed under aeroba conditions and the fungus gradually grows into the wood material where the availability of oxygen is probably considerably less. With the sandwich technique, the fungus material is introduced directly into the wood. The reduced supply of oxygen to the fungus, resulting from this method does not have a negative effect on the fungus—on the contrary, the sandwich principle has proved necessary for zoning. The fungus grows and produces zoning even deep down in a sandwich, whereas the conventional technique with inoculation of the wood surfaces results in only negligible zoning or none at all.

In one embodiment of the sandwich technique a block, sheet or the like of wood, plastic or paper, for instance, is placed on a single inoculated sheet of wood to be zoned.

Two methods which function in practice have been developed in order to control the pattern of zone lines to a certain extent:

1. Control by means of the inoculation procedure

Figure 4:
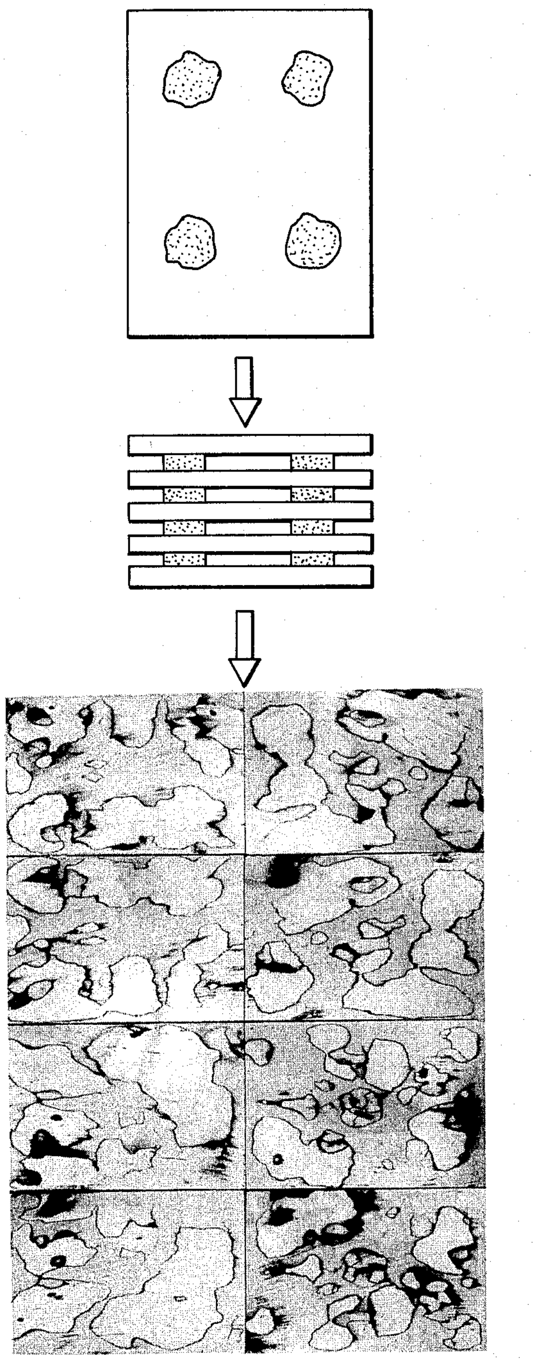

Provided the correct moisture content has been set in the wood, the zoning pattern can be affected by the manner in which the fungus suspension is inoculated onto the wood, which is thereafter incubated in accordance with the sandwich technique. FIGS. 4 and 5 show two examples of inoculation methods, point and streak inoculation, on 2 mm birch, and the result on mounted, ground and varnished sheets. Note that the sheets in a sandwich give a zoning pattern of pairs of mirror-images as shown in FIG. 4 and FIG. 6.

Inoculation may be performed with the aid of spray nozles with a rotating roller printing out a certain pattern by immersion of the wood in the fungus suspension using moisture-retaining, fungus-infected interlayers.

The inoculation pattern can be combined with impregnation by substances preventing the fungus from attacking the wood as described above.

Inoculation may be carried out using either one or several fungus cultures. In the latter case the cultures may be either of different types of fungus or different branches of the same type.

2. Control by moisture distribution

The moisture content in the wood is of fundamental importance for the zoning process. This can be exploited to control zoning by the method shown in FIG. 7 in which interlayers containing moisture are placed in a sandwich. In FIG. 7, 5 denotes inoculation material, 6 a sheet of wood and 7 an interlayer. The interlayer may be impregnated, e.g. with water nutrient or pH-controlled/redox-active substances and/or infected with inoculation material.

Another variant is for the interlayers to be dry and the sheets of wood moist, in order to obtain a moisture gradient in the wood. The sandwich with or without interlayers is preferably provided with weights to ensure satisfactory contact between wood and interlayer(s). Other forms of compression are also feasible.

With a correctly adjusted moisture content and inoculation volume, a zoning pattern having the appearance shown in FIG. 8 can be obtained. In FIG. 8, 8 denotes an interlayer and 9 a zone line. An example of a mounted sheet of this type is shown in FIG. 9. In this case a square interlayer has been used, but interlayers of other geometrical shapes are also possible. The zone lines travel up to the surface of the wood contacting the edges of the interlayer. Otherwise the zoning appears only partially, but a pattern of zone lines will be revealed when the wood is ground (FIG. 9). Another example of network patterning on a ground surface is shown in FIG. 10.

Conventional methods of incubating inoculated wood generally entail the wood being placed on sterile, moist vermiculite, earth, etc. Equilibrium is thus gradually achieved between the moisture in wood, supporting surface and air. As the wood is attacked by the fungus, the moisture content in the wood will generally increase. According to the present invention, the moisture content is set in he wood at the start (see above) and the wood is thereafter incubated in a completely closed system with 100% relative humidity but without a moist supporting surface. Fluctuations in the moisture content of the wood are thus avoided, which in a thin wood material might easily lead to the fungus not growing normally. A closed system also gives better protection against infection and the composition of the gas atmosphere can easily be controlled. The content of oxygen and carbon dioxide and the occurrence of light provide a method of controlling both the growth of the fungus and the zoning of the wood.

Zoning starts to appear after 3–4 weeks' incubation but at least 6–8 weeks' incubation is desirable to ensure a satisfactory result. The incubation time required is also dependent on the thickness of the wood and the desired penetration depth of the zoning. In thin veneer, zone lines penetrating right through the wood can be obtained in about 6 weeks.

It is important that the wood and the fungus material are protected against infection, particularly at the start of the process. Particularly problematical are infections by mould fungi which often grow faster than higher fungi and overcome the latter. Spores of mould fungi also constitute a health hazard. To avoid infection the method claimed has the following characteristics.

- The inoculation material is produced under sterile conditions.
- Treatment and inoculation of the wood are performed under conditions as aseptic as possible.
- A large volume of active inoculation material is used, resulting in quicker establishment of the desired fungus and thus less risk of infection (and quicker zoning).
- Fungi are used such as *Armillaria mellea* which, besides producing zoning, also produce antibiotics and give the wood a certain automatic protection against infection.
- If necessary the wood may be pretreated with anti-mould composition such as Benomyl.
- Incubation can be performed in a completely closed system (see above).

When the desired zoning has been obtained the action of the fungus on the wood must be discontinued. This does not constitute any great problem and can easily be achieved by one of two methods:

- The sheets of wood are dried, whereupon the fungus is inactivated.
- Steam is conducted into the incubator, whereupon the fungus is killed; the wood is then dried.

Further features of the present invention appear in the following claims.

I claim:

1. A method of treating wood to effect zoning, comprising the steps of:

(a) pretreating the wood to disinfect the wood and to adjust the moisture content of the wood to a desired value;

(b) treating the wood to inhibit decomposition of the wood by fungus, while allowing fungus growth therein by impregnating the wood with a nutrient solution;

(c) inoculating the pretreated and treated wood with at least one fungus culture; and (d) incubating the inoculated wood under controlled conditions to obtain zoning, in the substantial absence of decomposition of the wood.

2. A method according to claim 1, wherein said pretreatment comprises treating with antimicrobial substances.

3. A method according to claim 1, wherein the moisture content is adjusted by the addition of a controlled quantity of water which is absorbed and distributed in the wood.

4. A method according to claim 1, wherein said fungus culture is inoculated on said wood in a pattern.

5. A method according to claim 1, wherein parts of the wood are in contact with water, moist vermiculite, or moist sawdust.

6. A method according to claim 1, wherein said step of incubating is carried out in air saturated with water vapor to achieve substantially uniform moisture content in said wood.

7. A method according to claim 1, wherein the growth of fungus during said incubating step is controlled by regulating the oxygen, carbon dioxide, moisture and/or light to which said fungus is exposed.

8. A method according to claim 1, wherein said step of incubating comprises first, carrying out said incubating under optimal conditions for fungus growth; and subsequently, carrying out said incubating under optimal conditions for zoning.

9. A method according to claim 1, wherein at least one of the steps of pretreatment, treatment and inoculation is performed at least partially in a closed system.

10. A substantially non decomposed zoned wood, produced according to the method of claim 1.

11. A method according to claim 1, additionally comprising treating said wood with a substance which stimulates the ability of fungi to form zones and which controls the appearance of said zones, said substance being a nutrient for the fungus culture.

12. A method according to claim 1, additionally comprising treating said wood with a substance which stimulates the ability of fungi to form zones and which controls the appearance of said zones, said substance being a pH control agent.

13. A method according to claim 1, wherein said step of treating comprises impregnating said wood with a substance which promotes the growth of fungi to induce rapid establishment of the fungi and to insure that the fungi are sustained by the impregnated substance and not by the wood.

14. A method according to claim 13, wherein said impregnating substance comprises a pH control agent.

15. A method according to claim 1, additionally comprising treating a portion of said wood with a substance which prevents fungi from growing on said wood, in order to direct said zoning to other parts of said wood.

16. A method according to claim 15, wherein said treating substance is selected from the group consisting of hydrophobic substances and inhibitors.

17. A method according to claim 1, wherein said fungus culture produces antibiotics, and provides protection against infection to the wood.

18. A method according to claim 17, wherein said fungus culture is *Armillaria mellea.*

19. A method according to claim 1, wherein said step of inoculating is performed by spraying said fungus culture on said wood in a pattern.

20. A method according to claim 19, wherein said pattern is dots or streaks.

21. A method according to claim 1, additionally comprising inoculating a plurality of pieces of said wood, and stacking said pieces in sandwich fashion for said incubating step.

22. A method according to claim 21, wherein said interlayer is formed from wood, sawdust, cardboard, plastic or vermiculite.

23. A method according to claim 21, wherein at least one piece of said wood is moist.

24. A method according to claim 21, wherein an interlayer is inserted between two pieces of said wood, to produce a zoning pattern.

25. A method according to claim 24, wherein said interlayer is dry, is impregnated with water, is impregnated with at least one substance which controls growth or zoning of said fungi, or has been previously inoculated and permeated by fungi.

26. A method according to claim 24, wherein at least one piece of said wood is moist.

* * * * *